US00PP33766P2

(12) United States Plant Patent
Lintott

(10) Patent No.: US PP33,766 P2
(45) Date of Patent: Dec. 21, 2021

(54) ***LEUCANTHEMUM* PLANT NAMED 'REAL GOLDCUP'**

(50) Latin Name: ***Leucanthemum* x *superbum***
Varietal Denomination: Real Goldcup

(71) Applicant: Jennifer Muriel Lintott, Bognor Regis (GB)

(72) Inventor: Keith George Lintott, Bognor Regis (GB)

( * ) Notice: Subject to any disclaimer, the term of this patent is extended or adjusted under 35 U.S.C. 154(b) by 0 days.

(21) Appl. No.: 17/377,371

(22) Filed: Jul. 15, 2021

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
CPC ..... A01H 6/14; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new cultivar of *Leucanthemum* plant named 'Real Goldcup' that is distinguishable by upright plant habit, long narrow dentate leaves and inflorescences consisting of two to three whorls of bright yellow ray florets arranged horizontally, the bright yellow color of the ray florets persists and only fades to pale yellow with the onset of senescence, flowering of 'Real Goldcup' commences in late June or early July and continues until October, is disclosed.

2 Drawing Sheets

Genus and species: *Leucanthemum* x *superbum*.
Variety denomination: 'Real Goldcup'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Goldcup'. *Leucanthemum* is a genus within the family Asteraceae in which the commonly referred to "flower" is botanically the inflorescence which is comprised of outer showy ray florets surrounding smaller disc florets.

'Real Goldcup' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Goldcup' is a seedling selection that resulted from the controlled pollination in 2009 of a single plant of the inventors' proprietary *Leucanthemum* seedling 'L9012-2' (unreleased and unpatented) as the female parent, using pollen from a single plant of the inventors' proprietary *Leucanthemum* seedling 'L1122-15' (unreleased and unpatented) as the male parent. The inventors selected 'Real Goldcup' in 2012 for its combination of tight clumping basal branching and upright habit, numerous yellow inflorescences with bright yellow ray florets arranged around an orange-yellow central disc.

'Real Goldcup' was first asexually propagated by the inventors in West Sussex, United Kingdom in 2014 using the method of vegetative division and subsequently by basal shoot cuttings. Since that time under careful observation 'Real Goldcup' has been determined uniform, stable and true to type in subsequent generations of asexual propagation.

SUMMARY

The following traits have been repeatedly observed and represent the distinguishing characteristics of 'Real Goldcup'. In combination, these traits set 'Real Goldcup' apart from all other existing varieties of *Leucanthemum* known to the inventor. 'Real Goldcup' has not been tested under all possible conditions and phenotypic differences may be observed with variations in environmental, climatic, and cultural conditions.

1. 'Real Goldcup' exhibits an upright plant habit.
2. The foliage of 'Real Goldcup' is long and narrow with dentate margins.
3. A fully expanded inflorescence of 'Real Goldcup' is 7 cm. in diameter and is comprised of ray florets arranged around a large central disc.
4. The ray florets of 'Real Goldcup' are arranged in 2 to 3 concentric whorls.
5. The ray florets of 'Real Goldcup' are bright yellow in color and are arranged horizontally when fully expanded.
6. The ray florets of 'Real Goldcup' maintain their bright yellow color throughout flowering until senescence when the ray florets fade to pale-yellow in color.

7. The central disc of the inflorescence of 'Real Goldcup' appears as a cushion comprised of orange-yellow colored disc florets.
8. The inflorescences of 'Real Goldcup' are carried on a strong, stiff stems.
9. Flowering of 'Real Goldcup' commences in late June or early July and continues until October.
10. After one year of growth in a 2-gallon container, or planted in the ground, a plant of 'Real Goldcup' is 40 cm to 45 cm in height and 25 cm to 30 cm in width.
11. 'Real Goldcup' is hardy in USDA Zone 5 (−20° F. or −28° C.).

COMPARISON WITH PARENTAL LINES AND KNOWN VARIETY

In comparison with the female parent, seedling 'L9012-2', 'Real Goldcup' exhibits greater plant vigor and is later to flower. In addition, the inflorescences of 'Real Goldcup' are smaller than the inflorescences of the female parent, and the central disc of 'Real Goldcup' is larger than the central disc of the female parent. In comparison with the male parent, seedling 'L1122-15', 'Real Goldcup' exhibits greater plant vigor and grows with a more upright plant habit and is later to flower. In addition, the ray florets of 'Real Goldcup' are bright yellow in color, whereas the ray florets of the male parent are lemon-colored.

The commercial variety of *Leucanthemum* which the inventors consider to most closely resemble 'Real Goldcup' is *Leucanthemum* Plant Named 'Leumayel' (U.S. Plant Pat. No. 19,242) also known as 'Broadway Lights'. In comparison with leumayer, plants of 'Real Goldcup' are later to flower and bear bright yellow ray florets which persist in that color until senescence when the ray florets become pale yellow in color. The ray florets of 'Leumayel' are yellow in color when opening, then fading to soft pale yellow and then to white as they age.

BRIEF DESCRIPTION OF THE PHOTOGRAPHS

The accompanying color photographs were taken in July 2018 in Oxnard, Calif. The photographs illustrate the overall appearance of 'Real Goldcup' showing the color of foliage and inflorescence as true as is reasonably possible to obtain in color reproductions of this type. The illustrated plants have been grown out of doors in Oxnard, Calif. without any pruning or use of chemical growth regulators. The colors in the photographs may differ from color values cited in the detailed botanical description, which accurately describe the actual color of 'Real Goldcup'.

BOTANICAL DESCRIPTION OF THE PLANT

Figure 1:
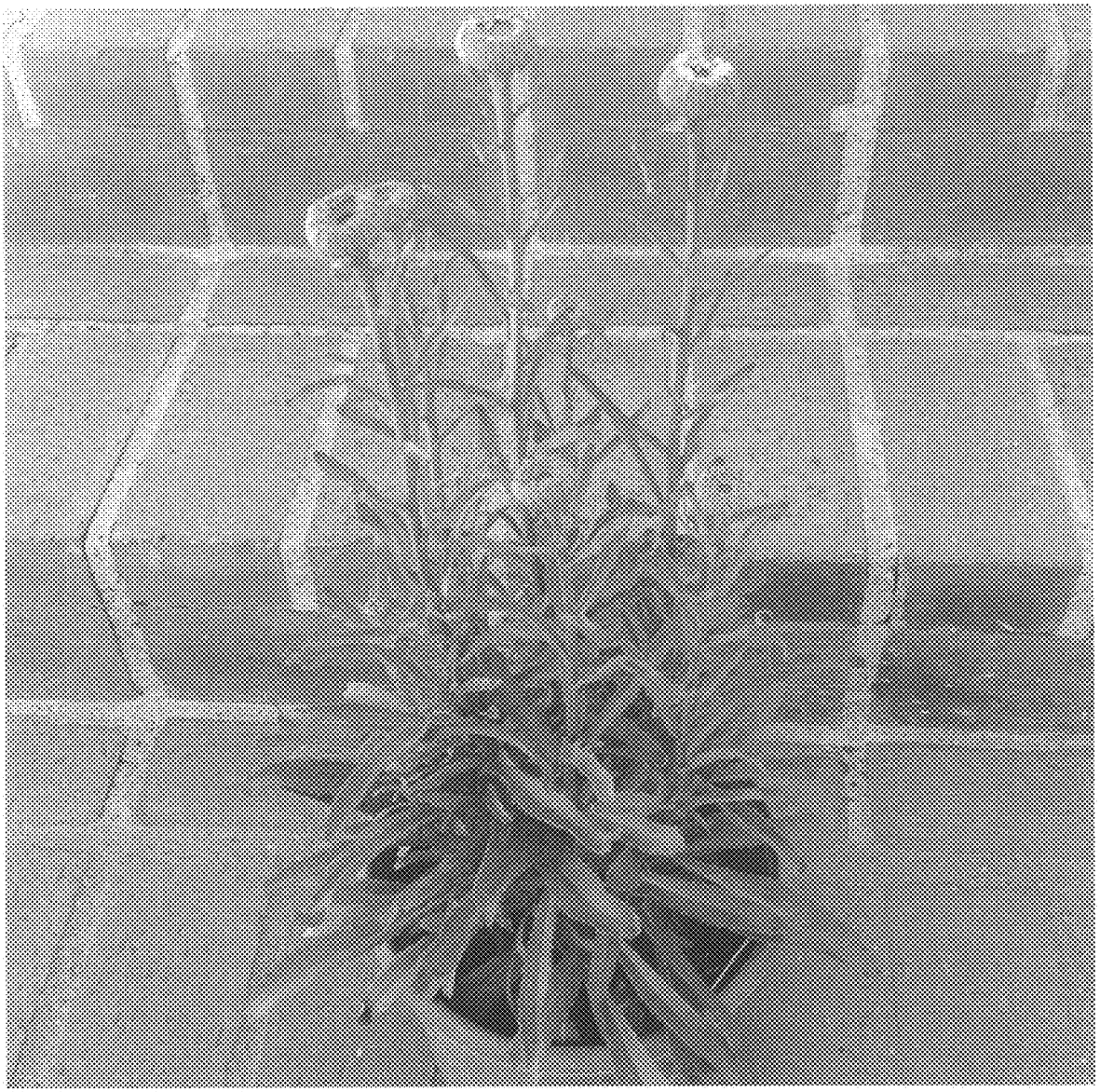
FIG. 1 illustrates a one-year-old plant of 'Real Goldcup' when in bud.
Figure 2:
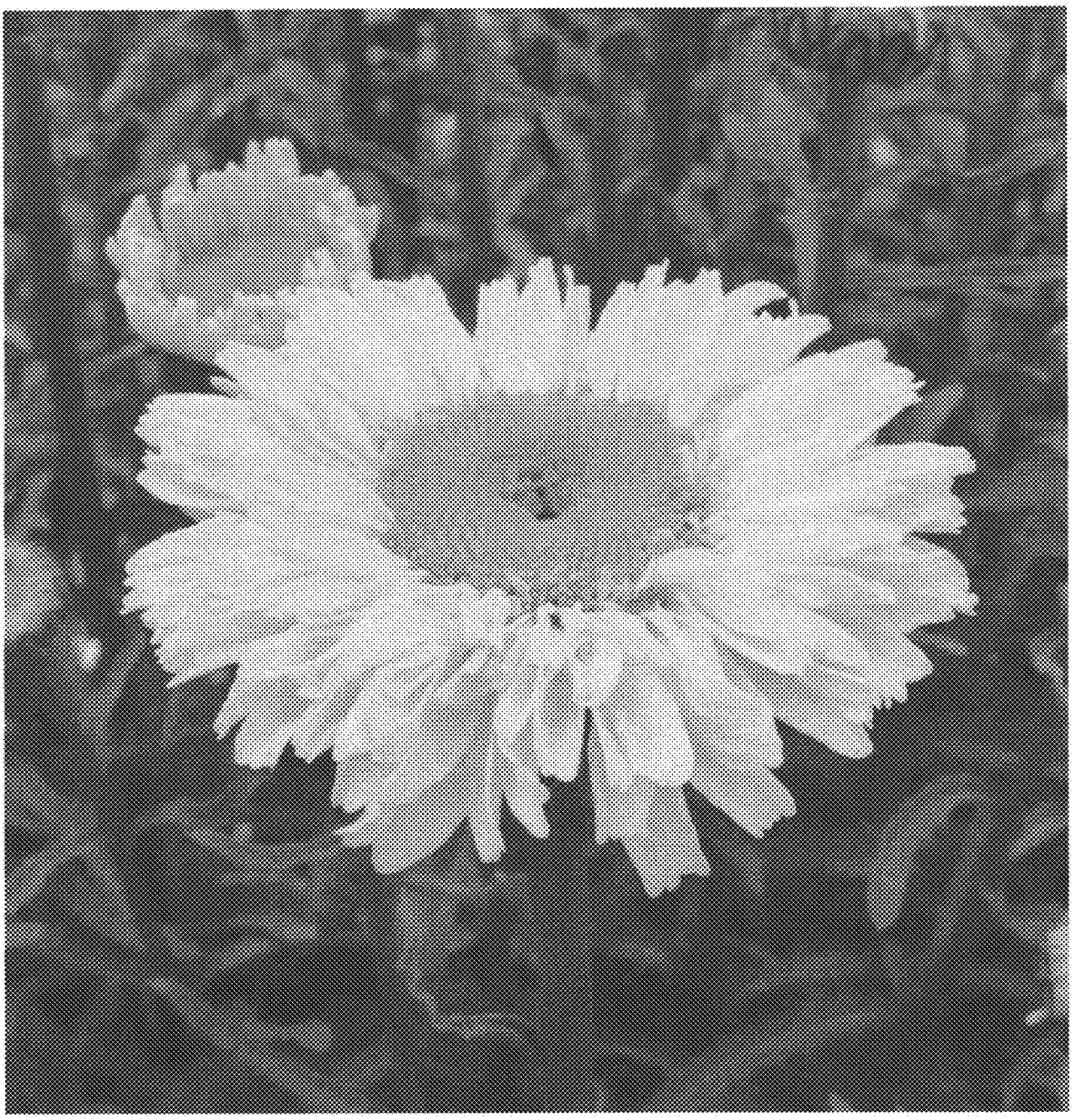
FIG. 2 illustrates a close-up of the inflorescence of 'Real Goldcup'.

The following is a detailed botanical description of the new cultivar 'Real Goldcup'. Observations, measurements, values and comparisons were collected in Santa Barbara, Calif. during late June and early July 2021, from a 1-year-old plant growing outdoors in a 2-gallon container. Color determinations are made in accordance with The 2007 Royal Horticultural Society Colour Chart from London, England, except where general color terms of ordinary dictionary significance are used.

Botanical classification:

*Family.*—Asteraceae (formerly Compositae).

*Genus.*—*Leucanthemum.*

*Species.*—x *superbum.*

*Denomination.*—'Real Goldcup'.

*Common name.*—Shasta daisy.

*Habit.*—Upright growth habit.

*Commercial category.*—Perennial.

*Use.*—For garden and landscape.

*Suggested commercial container size.*—1-gallon, 2-gallon containers.

*Parentage.*—*Leucanthemum* x *superbum* 'Real Goldcup' is a seedling selection resulting from the controlled cross-pollination of the following parents: Female parent: *Leucanthemum* seedling 'L9012-2'. Male parent: *Leucanthemum* seedling 'L1122-15'.

*Propagation method.*—Basal shoot cuttings, division, tissue culture.

*Rooting system.*—Fine and fibrous.

*Vigor.*—Moderate.

*Time to develop roots* (*range*).—14 to 20 days are needed for an initial cutting to develop roots.

*Temperature to develop roots* (*range*).—The recommended air temperature is 20° C. to 21° C.

*Crop time* (*range*).—7 to 8 months to produce a flowering plant in a 1-gallon container starting from a rooted cutting. 10 months to produce a full plant in a 2-gallon container. A plug or liner (starter plant) may be finished in 10 to 14 weeks.

*Plant dimensions* (*one year*).—Plant height 40 cm to 45 cm. including the flowers which are held 15 cm to 20 cm above the foliage canopy; plant diameter 25 cm to 30 cm.

*Cultural requirements.*—Grow in full sun and rich, moist moderately fertile well-draining soil.

*Pest or disease resistance and susceptibility.*—No specific disease or pest resistance or susceptibility has been observed.

*Hardiness.*—USDA Zone 5.

Stems, branches: Stems arise from base and bear terminal inflorescences.

*Branching.*—Basal and lateral.

*Basal branches.*—Quantity: Initially (first flush of growth): 7. Dimensions: Length, 25 cm; diameter at base 0.6 cm. Shape: Cylindrical. Color: 143C with longitudinal streaks 143C and 181C towards base. Surface: Pubescent, hairs fine, white NN155D, up to 1 mm in length. Strength: Strong, stiffly upright.

*Lateral branches.*—Arrangement: Present in opposite pairs arising in lower leaf nodes. Quantity: 16 to 20. Dimensions: Length 20 cm. when flowering; diameter at base 0.4 cm. Shape: Cylindrical. Color: 143C with longitudinal streaks 143C and 181C towards base. Surface: Pubescent, hairs fine, white NN155D, up to 1 mm in length. Strength: Strong, stiffly upright.

Foliage:

*Type* (*division*).—Simple. Leaflets emerge at lower stem nodes only.

*Leaf arrangement.*—Alternate.

*Internode distance* (*range*).—2.0 cm to 2.5 cm.

*Leaf margin.*—Mostly regularly dentate; teeth 0.5 mm to 1.5 mm in length, angled towards leaf apex, spaced at 3 mm to 4 mm. intervals.

*Leaf apex.*—Rounded and adaxially inwardly cupped.

*Leaf base.*—Attenuate.
*Leaf attachment.*—Sessile.
*Leaf color* (*adaxial surface*).—137B.
*Leaf color* (*abaxial surface*).—137D.
*Leaf shape.*—Lanceolate.
*Leaf dimensions* (*lower, oldest, leaves*).—14 cm in length, 2.3 cm in width.
*Leaf dimensions* (*upper, newest, leaves*).—3.5 cm in length, 0.5 cm in width.
*Leaf venation.*—Pinnate, but very faint.
*Leaf vein color* (*both surfaces*).—As leaf color, 137B (adaxial), 137D (abaxial) surfaces except midrib (both surfaces) 144B.
*Leaf surface* (*adaxial surface*).—Smooth, glossy, iridescent.
*Leaf surface* (*abaxial surface*).—Smooth, semi-glossy.
*Leaflet arrangement.*—Opposite.
*Leaflet dimensions.*—Up to 2 cm in length, 3 mm in width.
*Leaflet apex.*—Acute.
*Leaflet base.*—Truncate.
*Leaflet color* (*both surfaces*).—143C.
*Leaflet veins.*—None visible.
*Leaflet surface* (*both surfaces*).—Smooth, glossy.

Inflorescence:
*Inflorescence type.*—Capitulum, consisting of ray florets and disc florets.
*Inflorescence quantity.*—Initially 10 to 15 buds and flowers during first flush of flowering, increasing by mid-summer to 30 to 35 buds and flowers when lateral branches bear flowers.
*Inflorescence diameter* (*fully opened*).—7 cm.
*Inflorescence depth.*—3 cm to 4 cm.
*Inflorescence aspect.*—Upright. Ray florets upright when emerging becoming horizontal when fully developed.
*Inflorescence colors* (*when fully developed*).—Ray florets: 9A fading to 4D at onset of senescence. Disc: 24A.
*Fragrance.*—None.
*Blooming season.*—Late June or early July until October.
*Lastingness of inflorescence* (*range*).—14 days on the plant, 7 to 10 days as a cut flower.

Bud: Bud dimensions 0.8 cm in height and 2 cm in diameter.
*Bud shape.*—Oblate spheroid.
*Bud color.*—143C (cluster of juvenile involucral bracts with bract margins 187B).
*Bud surface.*—Smooth, semi-glossy.

Peduncle: Each basal and lateral stem bears terminal inflorescence. Peduncle description applies to section of stem between uppermost leaf node and base of inflorescence.
*Dimensions.*—Length 10 mm to 15 mm; diameter 4 mm (lateral branches), 6 mm (basal branches).
*Shape.*—Cylindrical.
*Color.*—143C with longitudinal streaks 143C and 181C towards base.
*Surface.*—Pubescent, hairs fine, white NN155D, up to 1 mm in length.

Peduncle Bracts: Absent.

Ray florets:
*Ray floret arrangement.*—Acropetalous in 2 to 3 whorls.
*Shape.*—Uppermost whorl: ray florets quilled. Otherwise, strap-like, longitudinally furrowed.
*Quantity.*—60 to 70 ray florets per inflorescence.
*Aspect.*—Radiate, emerging vertically becoming horizontal when fully developed.
*Corolla tube dimensions.*—5 mm in length, 1 mm in diameter.
*Corolla tube color.*—1D.
*Ray floret petals.*—Surface (both surfaces): Glabrous. Apex: Emarginate (4-lobed to 5-lobed). Margin: Entire. Dimensions: 30 mm in length (including corolla tube), inner ray florets 8 mm. in width, otherwise 10 mm to 12 mm in width. Color (both surfaces): 9A fading to 4D.

Involucral bracts:
*Quantity* (*average*).—35 to 40 per inflorescence, arranged in two overlapping whorls, fused at the base.
*Bract color* (*abaxial and adaxial surfaces*).—143C.
*Bract length.*—5 mm to 8 mm.
*Bract width.*—2 mm.
*Bract apex.*—Rounded.
*Bract base.*—Truncate.
*Bract surface* (*both surfaces*).—Glabrous.
*Bract shape.*—Lanceolate.
*Bract margin.*—Entire, smooth, color 187B.

Disc florets:
*Disc diameter.*—3 cm.
*Disc floret quantity* (*average*).—Approximately 400 to 450 per inflorescence.
*Disc color.*—24A.
*Disc floret dimensions.*—6 mm in length, 1 mm in diameter.
*Disc floret shape.*—Tubular.
*Disc floret petals.*—Quantity: Ranges from 3 to 5 in number, basally fused. Dimensions, (including corolla tube): 3 mm in length, 0.75 mm in width. Color (both surfaces): 24A; corolla tube 151D (both surfaces). Apex: Acute. Base: Truncate.

Reproductive organs:
*Ray florets.*—Androecium (stamens, anthers, filaments, pollen): Absent. Pistil: 1, 3 mm in length, hair-like, diameter less than 0.2 mm., color light brown. Stigma: 2 mm in length, hair-like, diameter less than 0.2 mm, color light brown. Ovary (observed immature only): Superior, globose, less than 1 mm in diameter, color 145C.
*Disc florets.*—Stigma, style, and ovary not observed. Stamens: 5, fused appearing as one, length 1 mm, color 175A. Pollen: None observed. Pistil: 1, less than 1 mm in length, stigma, style, ovary not observed.
*Seed.*—None observed.

I claim:

1. A new and distinct cultivar of *Leucanthemum* plant named 'Real Goldcup' as described and illustrated herein.

* * * * *